(12) United States Patent
Kim et al.

(10) Patent No.: US 7,209,785 B2
(45) Date of Patent: *Apr. 24, 2007

(54) APPARATUS AND METHOD FOR R-WAVE DETECTION WITH DUAL DYNAMIC SENSITIVITIES

(75) Inventors: Jaeho Kim, Redmond, WA (US); Joseph M. Bocek, Seattle, WA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 593 days.

This patent is subject to a terminal disclaimer.

(21) Appl. No.: 10/608,518

(22) Filed: Jun. 24, 2003

(65) Prior Publication Data

US 2004/0015192 A1    Jan. 22, 2004

Related U.S. Application Data

(63) Continuation of application No. 09/828,461, filed on Apr. 6, 2001, now Pat. No. 6,584,350.

(51) Int. Cl.
*A61N 1/39* (2006.01)

(52) U.S. Cl. ........................................................ 607/5

(58) Field of Classification Search ..................... 607/5
See application file for complete search history.

(56) References Cited

U.S. PATENT DOCUMENTS

| | | | |
|---|---|---|---|
| 5,207,219 A | 5/1993 | Adams et al. | 128/419 D |
| 5,282,836 A | 2/1994 | Kreyenhagen et al. | 607/4 |
| 5,395,373 A | 3/1995 | Ayers | 607/8 |
| 5,411,524 A | 5/1995 | Rahul | 607/4 |
| 5,480,413 A | 1/1996 | Greenhut et al. | 607/14 |
| 5,486,198 A | 1/1996 | Ayers et al. | |
| 5,545,182 A | 8/1996 | Stotts et al. | |
| 5,554,174 A | 9/1996 | Causey, III | 607/5 |
| 5,562,709 A * | 10/1996 | White | 607/5 |
| 5,584,864 A | 12/1996 | White | |
| 5,591,215 A | 1/1997 | Greenhut et al. | 607/14 |
| 5,674,250 A | 10/1997 | de Coriolis et al. | 607/7 |
| 5,709,215 A | 1/1998 | Perttu et al. | 128/708 |
| 5,776,164 A | 7/1998 | Ripart | 607/5 |
| 5,778,881 A | 7/1998 | Sun et al. | 128/696 |
| 5,814,081 A * | 9/1998 | Ayers et al. | 607/5 |
| 5,840,079 A | 11/1998 | Warman et al. | 607/4 |
| 5,853,426 A | 12/1998 | Shieh | 607/5 |
| 5,865,838 A | 2/1999 | Obel et al. | 607/5 |
| 5,968,079 A | 10/1999 | Warman et al. | |
| 5,987,354 A | 11/1999 | Cooper et al. | 607/5 |
| 5,991,657 A | 11/1999 | Kim | |
| 5,999,850 A | 12/1999 | Dawson et al. | 607/4 |
| 6,047,210 A | 4/2000 | Kim et al. | |
| 6,058,327 A * | 5/2000 | Borgerding et al. | 607/9 |
| 6,081,745 A | 6/2000 | Mehra | 607/4 |
| 6,081,746 A | 6/2000 | Pendekanti et al. | |
| RE36,765 E | 7/2000 | Mehra | 607/4 |
| 6,085,116 A | 7/2000 | Pendekanti et al. | 607/5 |
| 6,091,988 A | 7/2000 | Warman et al. | 607/5 |
| 6,161,037 A | 12/2000 | Cohen | 600/513 |
| 6,246,906 B1 | 6/2001 | Hsu et al. | |
| 6,249,699 B1 | 6/2001 | Kim | |
| 6,249,701 B1 * | 6/2001 | Rajasekhar et al. | 607/9 |
| 6,272,380 B1 | 8/2001 | Warman et al. | 607/5 |
| 6,459,932 B1 | 10/2002 | Mehra | 607/5 |
| 6,512,951 B1 | 1/2003 | Marcovecchio et al. | |
| 6,584,350 B2 * | 6/2003 | Kim et al. | 607/5 |
| 6,847,842 B1 | 1/2005 | Rodenhiser et al. | |

* cited by examiner

*Primary Examiner*—Carl Layno
(74) *Attorney, Agent, or Firm*—Schwegman, Lundberg, Woessner, Kluth, P.A.

(57) ABSTRACT

An apparatus and method for delivering electrical shock therapy in order to treat atrial tachyarrhythmias such as fibrillation utilizes a dynamically varying threshold to detect R-waves and synchronously deliver a defibrillation shock.

17 Claims, 2 Drawing Sheets

APPARATUS AND METHOD FOR R-WAVE DETECTION WITH DUAL DYNAMIC SENSITIVITIES

CROSS-REFERENCE TO RELATED APPLICATION(S)

This application is a continuation of U.S. patent application Ser. No. 09/828,461, filed on Apr. 6, 2001, now issued as U.S. Pat. No. 6,584,350, the specification of which is incorporated herein by reference.

FIELD OF THE INVENTION

This invention pertains to methods for treating atrial tachyarrhythmias. In particular, the invention relates to an apparatus and method for delivering shock therapy to terminate atrial fibrillation.

BACKGROUND

Tachyarrhythmias are abnormal heart rhythms characterized by a rapid heart rate, typically expressed in units of beats per minute (bpm). They can occur in either chamber of the heart (i.e., ventricles or atria) or both. Examples of tachyarrhythmias include sinus tachycardia, ventricular tachycardia, ventricular fibrillation (VF), atrial tachycardia, and atrial fibrillation (AF). Tachycardia is characterized by a rapid rate, either due to an ectopic excitatory focus or abnormal excitation by normal pacemaker tissue. Fibrillation occurs when the chamber depolarizes in a chaotic fashion with abnormal depolarization waveforms as reflected by an EKG.

Cardioversion (an electrical shock delivered to the heart synchronously with an intrinsic depolarization) and defibrillation (an electrical shock delivered without such synchronization) can be used to terminate most tachyarrhythmias by depolarizing excitable myocardium, which thereby prolongs refractoriness, interrupts reentrant circuits, and discharges excitatory foci. As used herein, the term defibrillation should be taken to mean an electrical shock delivered either synchronously or not in order to terminate a fibrillation. Implantable cardioverter/defibrillators (ICDs) provide this kind of therapy by delivering a shock pulse to the heart when fibrillation is detected by the device. An ICD is a computerized device containing a pulse generator that is usually implanted into the chest or abdominal wall. Electrodes connected by leads to the ICD are placed on the heart, or passed transvenously into the heart, to sense cardiac activity and to conduct the shock pulses from the pulse generator. ICDs can be designed to treat either atrial or ventricular tachyarrhythmias, or both, and may also incorporate cardiac pacing functionality.

The most dangerous tachyarrhythmias are ventricular tachycardia and ventricular fibrillation, and ICDs have most commonly been applied in the treatment of those conditions. ICDs are also capable, however, of detecting atrial tachyarrhythmias, such as atrial fibrillation and atrial flutter, and delivering a shock pulse to the atria in order to terminate the arrhythmia. Although not immediately life-threatening, it is important to treat atrial fibrillation for several reasons. First, atrial fibrillation is associated with a loss of atrio-ventricular synchrony which can be hemodynamically compromising and cause such symptoms as dyspnea, fatigue, vertigo, and angina. Atrial fibrillation can also predispose to strokes resulting from emboli forming in the left atrium. Although drug therapy and/or in-hospital cardioversion are acceptable treatment modalities for atrial fibrillation, ICDs configured to treat atrial fibrillation offer a number of advantages to certain patients, including convenience and greater efficacy.

As aforesaid, an ICD terminates atrial fibrillation by delivering a shock pulse to electrodes disposed in or near the atria. The resulting depolarization also spreads to the ventricles, however, and there is a risk that such an atrial shock pulse can actually induce ventricular fibrillation, a condition much worse than atrial fibrillation. To lessen this risk, current ICDs delay delivering an atrial shock pulse until the intrinsic ventricular rhythm is below a specified maximum rate and then deliver the shock synchronously with a sensed ventricular depolarization (i.e., an R-wave). That is, an R-R interval, which is the time between a presently sensed R-wave and the preceding R-wave, is measured. If the R-R interval is above a specified minimum value, the interval is considered shockable and the atrial defibrillation shock pulse is delivered.

Currently available implantable cardiac rhythm management devices, including bradycardia and tachycardia pacemakers and cardiac defibrillators, have sense amplifier circuits for amplifying and filtering electrogram signals picked up by electrodes placed in or on the heart and which are coupled by suitable leads to the implantable cardiac rhythm management device. In some devices, the signals emanating from the sense amplifier are applied to one input of a comparator circuit whose other input is connected to a source of reference potential. Only when an electrogram signal from the sense amplifier exceeds the reference potential threshold will it be treated as a detected cardiac depolarization event such as an R-wave or a P-wave. The source reference potential may thus be referred to as a sensing threshold. Other devices implement the comparator function in software such that a digitized electrogram signal value is compared with a reference value in order to detect the depolarization event.

When a sensing threshold is set to a constant value, malsensing of cardiac depolarization events can occur due to a number of factors. First, cardiac depolarization events can have widely different peak amplitudes, depending on patient activity body position, drugs being used, etc. Lead movement and noise may further affect the detection of cardiac depolarization events. Noise sources may include environmental noise, such as 60 Hz power line noise, myopotentials from skeletal muscle, motion artifacts, baseline wander and T-waves. When noise levels in the electrocardiogram approach the sensing threshold, the likelihood of oversensing increases (i.e., false detection of depolarization events). If the sensing threshold is increased too high in an attempt to overcome the effects of noise, on the other hand, the likelihood of undersensing (i.e., failing to detect depolarization events) is increased. Methods have therefore been developed to automatically adjust the sensing thresholds of cardiac rhythm management devices in accordance with sensed activity. Such methods, however, present special problems with respect to R-wave detection in atrial defibrillators.

SUMMARY OF THE INVENTION

The present invention is a method and apparatus for delivering atrial defibrillation shocks synchronously with R-waves detected using a dynamic threshold with two sensitivities. In order to lessen the probability of inducing ventricular fibrillation, an atrial defibrillation shock is delivered in synchrony with an R-wave that occurs after a specified shockable time interval has elapsed as measured from the preceding R-wave. In accordance with the invention, ventricular electrograms are sensed through a ventricular sensing channel, and a ventricular depolarization event (R-wave) is detected when a sensed ventricular electrogram value exceeds a threshold that dynamically varies in accordance with measured peak amplitudes. In order to provide an R-wave detector with a desirable higher sensitivity within a short interval after an R-wave is detected and with a higher specificity after the shockable time interval has elapsed, two additional thresholds are employed to detect R-waves for purposes of delivering an atrial defibrillation shock. A low shock threshold with a low value relative to the dynamically varying threshold is employed for detection immediately after an R-wave is detected and thereafter until the shockable time interval elapses. After the shockable time interval has elapsed, a high shock threshold with a high value relative to the dynamically varying threshold is used to detect a subsequent R-wave.

In an exemplary embodiment, a dynamically varying threshold for R-wave detection is provided as a threshold function that is set to a specified percentage of the peak value of each detected R-wave and then decays to a base value (e.g., decreases exponentially or linearly). Upon detecting an episode of atrial fibrillation or other atrial tachyarrhythmia, an atrial defibrillation shock is delivered synchronously when the dynamically varying threshold detects an event, the interval from the last event detected by the low shock threshold to the event presently detected by the dynamically varying threshold or the low shock threshold is greater than the shockable time interval, and the high shock threshold also detects an event within a specified time interval from the event detected by the low shock threshold or the dynamically varying threshold. The low shock threshold and the high shock threshold may be specified as percentages of a specified minimum value for the dynamically varying threshold.

DETAILED DESCRIPTION OF THE INVENTION

The present invention is a method and apparatus for delivering atrial defibrillation shock therapy. As used herein, atrial defibrillation shock therapy should be taken to mean shock therapy for treating any atrial tachyarrhythmia, such as atrial flutter, as well as atrial fibrillation.

Figure 1:
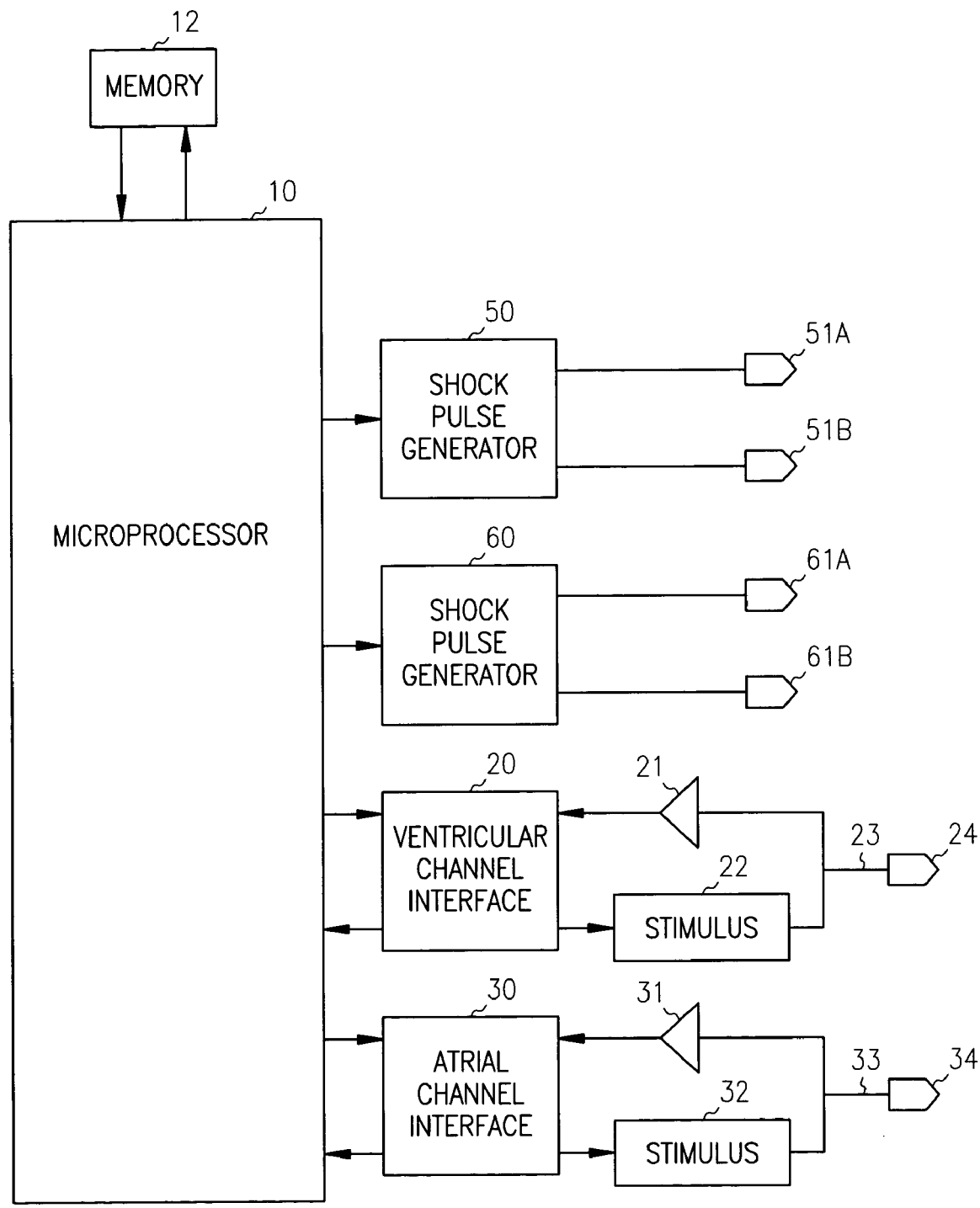
FIG. 1 is a system diagram of an implantable cardioverter/defibrillator.

FIG. 1 is a system diagram of a microprocessor-based implantable cardioverter/defibrillator device for treating atrial tachyarrhythmias that also incorporates a pacemaker functionality. In this embodiment, a microprocessor and associated circuitry make up the controller of the device, enabling it to output pacing or shock pulses in response to sensed events and lapsed time intervals. The microprocessor 10 communicates with a memory 12 via a bidirectional data bus. The memory 12 typically comprises a ROM or RAM for program storage and a RAM for data storage. The ICD has atrial sensing and pacing channels comprising electrode 34, lead 33, sensing amplifier 31, pulse generator 32, and an atrial channel interface 30 which communicates bidirectionally with a port of microprocessor 10. The ventricular sensing and pacing channels similarly comprise electrode 24, lead 23, sensing amplifier 21, pulse generator 22, and a ventricular channel interface 20. For each channel, the same lead and electrode are used for both sensing and pacing. The electrogram signals generated by the sensing amplifiers may either be fed to a comparator that inputs a digital signal to the microprocessor or digitized by an analog-to-digital converter and then input to the microprocessor. The gain of the amplifier in each sensing channel may be adjusted by the microprocessor via an automatic gain control input AGC in accordance with sense signal amplitudes and/or measured noise levels. The sensing channels are used to control pacing and for measuring heart rate in order to detect tachyarrhythmias such as fibrillation. The ICD detects an atrial tachyarrhythmia, for example, by measuring the atrial rate as well as possibly performing other processing on data received from the atrial sensing channel. A shock pulse generator 50 is interfaced to the microprocessor for delivering shock pulses to the atrium via a pair of terminals 51a and 51b that are connected by defibrillation leads to shock electrodes placed in proximity to regions of the heart. The defibrillation leads have along their length electrically conductive coils that act as electrodes for defibrillation stimuli. A similar shock pulse generator 60 and shock electrodes 61a and 61b are provided to deliver ventricular fibrillation therapy in the event of an induced ventricular fibrillation from atrial shock pulses. The shock pulse generators 50 and 60 include a capacitor that is charged from a battery with an inductive boost converter to deliver the shock pulse.

When ventricular fibrillation is detected, the ICD charges up the capacitor to a predetermined value for delivering a shock pulse of sufficient magnitude to convert the fibrillation (i.e., the defibrillation threshold). The capacitor is then connected to the shock electrodes disposed in the heart to deliver the shock pulse. Since ventricular fibrillation is immediately life threatening, these steps are performed in rapid sequence with the shock pulse delivered as soon as possible.

Atrial defibrillation shocks are also delivered by charging an energy storage capacitor once atrial fibrillation is detected. The delivery of the shock pulse in this situation, however, does not take place immediately. In order to avoid the possible induction of ventricular fibrillation, atrial defibrillation shocks should be delivered synchronously with a sensed R-wave and after a minimum pre-shock R-R interval. (The R-R interval is the time between the immediately preceding R-wave and the presently sensed R-wave, and an R-wave may be regarded as either a spontaneously occurring depolarization or a ventricular pace.) This is done because the ventricle is especially vulnerable to induction of fibrillation by a depolarizing shock delivered at a time too near the end of the preceding ventricular contraction (i.e., close to the T wave on an EKG). Delivering the shock synchronously with a sensed R-wave thus moves the shock away from the vulnerable period, but at a very rapid ventricular rhythm, the ventricular beats may be so close together that even synchronously delivered shocks may induce ventricular fibrillation. Shocking should therefore be delayed until the ventricular rhythm is slow enough to safely deliver the defibrillation pulse as determined by measuring the R-R interval. An R-R interval that meets a specified safety criterion for shocking is termed a shockable R-R interval. Before delivering an atrial shock, the ventricular rhythm is monitored by measuring the R-R interval associated with each sensed R-wave. If a sensed R-wave occurs at an R-R interval longer than a specified minimum limit value, the interval is considered shockable so that the sensed R-wave is safe to shock on. An atrial defibrillation shock is then delivered immediately so as to be practically synchronous with the sensed R-wave.

In order to reduce malsensing of R-waves, the sensitivity of the ventricular sensing channel may be automatically adjusted. In the device of FIG. 1, an automatic gain control inputs are provided for the sensing amplifiers that enable the controller to adjust the sensitivity of the sensing channels by changing the level of the electrogram signal generated by the sensing amplifiers. This type of sensitivity adjustment would normally be performed slowly over a long time period. A more rapid sensitivity adjustment may be implemented by providing a dynamically varying threshold for detecting R-waves such as shown in FIGS. 2A through 2D. Electrogram signals that exceed the dynamically varying threshold DVT are interpreted as R-waves. The threshold DVT is set to a specified percentage (e.g., 75%) of the measured peak amplitude of each detected R-wave and then decays (e.g., exponentially or linearly) to a base value. In this manner, the sensitivity of the channel may be adjusted automatically on a beat-to-beat basis to reflect changes in the measured signal level.

Figure 2A:
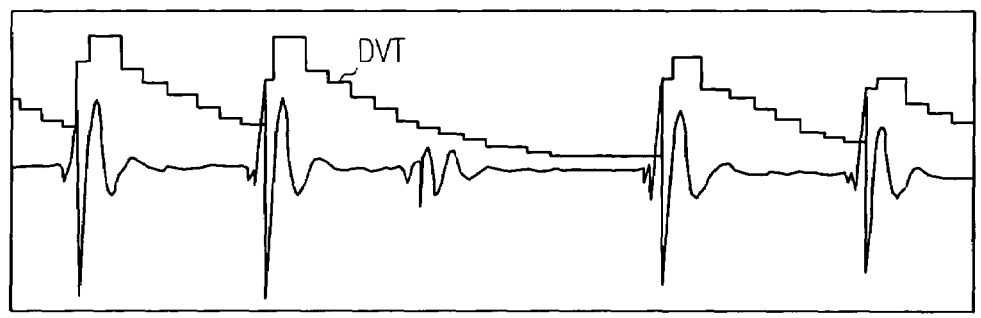
FIGS. 2A through 2D depict electrograms and exemplary threshold values for detecting R-waves.
Figure 2B:
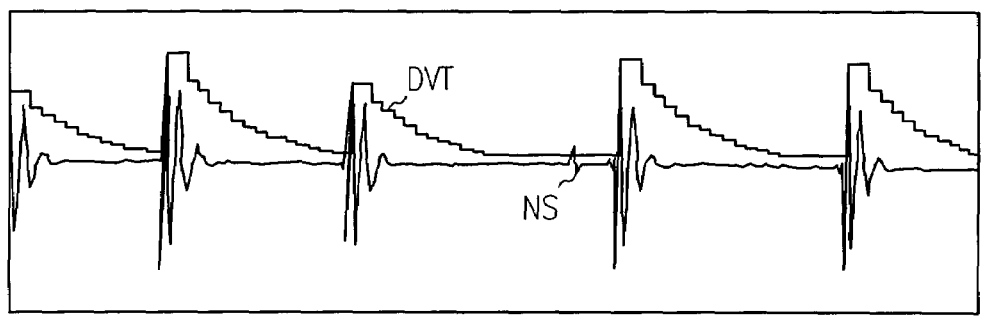

A problem with the dynamically varying threshold for R-wave detection as described above, however, is that the sensitivity of the channel is high during the interval shortly after an R-wave is detected and then subsequently decreases to a low level. This is not desirable behavior when R-waves are detected for the purpose of delivering an atrial defibrillation shock because if an R-wave is missed before the shockable interval after a detected R-wave elapses, there is a danger that the shock will be delivered in synchrony with a subsequently detected R-wave that does not meet the minimum shockable interval requirement. This is illustrated in FIG. 2A where small a amplitude R-wave is missed by the detector after a detected R-wave because the small R-wave does not exceed the dynamically varying threshold DVT. Also, during the time after the shockable time interval since the detected R-wave has passed, there is the possibility that an atrial shock pulse will be delivered in synchrony with a falsely detected R-wave, owing to the low value of the dynamically varying threshold. FIG. 2B illustrates this situation where a noise spike NS is interpreted as an R-wave because it exceeds the dynamically varying threshold DVT. Even if the shockable interval criterion is met at the time of the noise spike, it may still be clinically desirable to deliver the shock in synchrony with an actual R-wave. It is thus desirable for an R-wave detector used to deliver atrial defibrillation shocks to exhibit a high sensitivity when detecting R-waves for starting measurement of an R-R interval and to exhibit a high specificity when detecting R-waves for delivering a synchronous shock pulse. Prior devices have dealt with this problem by providing two R-wave detection channels, such as described in U.S. Pat. No. 5,562,709, assigned to Guidant Corp. and hereby incorporated by reference.

As aforesaid, the problems with using the dynamically varying threshold for detecting R-waves in order to deliver atrial defibrillation shocks are that of falsely negative detection shortly after a detected R-wave when the dynamically varying threshold is high and of falsely positive detection after the threshold has decayed to a low value. The present invention deals with this problem by providing two additional R-wave thresholds to be used for delivering atrial defibrillation shocks: a low shock threshold and a high shock threshold. The low shock threshold has a low value relative to the dynamically varying threshold and is employed for event detection after an R-wave is detected and before the shockable time interval elapses. This results in high sensitivity detection of depolarization events within a short interval after a first R-wave has been detected to lessen the possibility of missing such an event and shocking on a subsequently detected R-wave that did not occur after the minimum shockable time interval. After the shockable time interval has elapsed, the high shock threshold with a high value relative to the dynamically varying threshold is used to detect a subsequent R-wave for purposes of delivering a synchronous atrial defibrillation shock. This results in detection with the desired higher specificity in order to lessen the possibility of delivering a shock in synchrony with a falsely detected R-wave.

In accordance with the invention, an atrial defibrillation shock is thus delivered when three conditions are met: 1) the dynamically varying threshold detects an event, 2) the interval from the last event detected by the low shock threshold to the event presently detected by the low shock threshold or the dynamically varying threshold is greater than the shockable time interval, and 3) the high shock threshold also detects an event within a specified time interval from the event detected by the low shock threshold or the dynamically varying threshold. One means of implementing this scheme is to start a shockable interval timer when a sensed ventricular electrogram exceeds a specified low shock threshold value. An atrial defibrillation shock pulse is then delivered synchronously with a detected R-wave if the shockable interval timer has reached or exceeded a specified minimum value and if the sensed ventricular electrogram value exceeds both the dynamically varying threshold value and the specified high shock threshold value. The low shock threshold and the high shock threshold may be defined with respect to the minimum value that the dynamically varying threshold is allowed to have. For example, the low and high shock thresholds may specified as 200 and 500 percent, respectively, of the specified minimum value for the dynamically varying threshold.

Figure 2C:
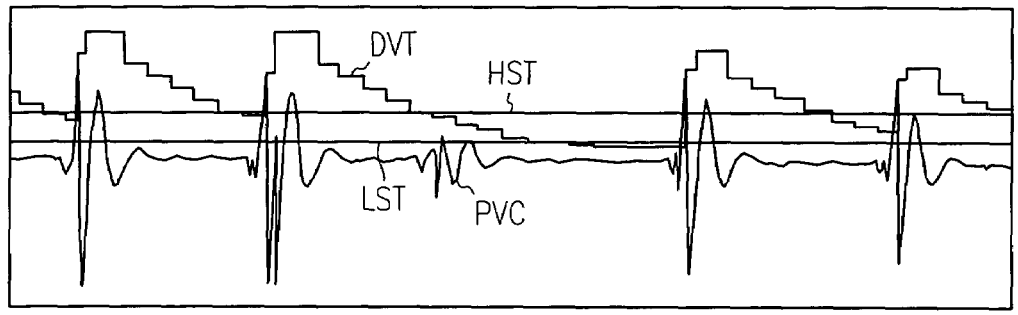
Figure 2D:
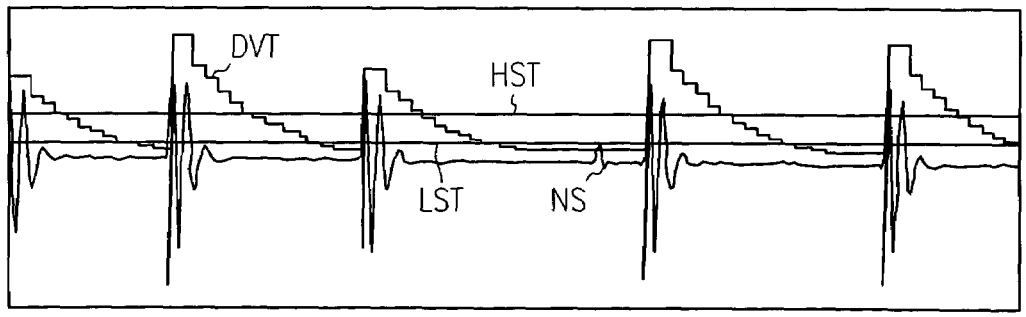

FIG. 2C illustrates an example in which a premature ventricular contraction (PVC) is detected by the low shock threshold LST where it would have been missed if only the dynamically varying threshold DVT were used. FIG. 2D shows a noise spike NS occurring after the minimum shockable interval. The noise spike exceeds the dynamically varying threshold DVT but does not exceed the high shock threshold HST. Therefore, no atrial defibrillation pulse is delivered.

The invention as described above may be implemented either with discrete hardware components or with software executed by a microprocessor. It should also be noted that the method would not disturb any algorithms for detecting ventricular tachyarrhythmias using the dynamically varying threshold. That is, when detecting R-waves for purposes other than delivering atrial defibrillation shocks, only the dynamically varying threshold can be used without regard to the low and high shock threshold values.

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for delivering atrial defibrillation therapy, comprising:
    detecting an episode of atrial fibrillation or other atrial tachyarrhythmia;
    detecting ventricular depolarizations (R-waves) with a ventricular sensing channel, wherein R-waves are detected when a sensed ventricular electrogram value exceeds a dynamically varying threshold value, wherein the dynamically varying threshold value is set to a specified percentage of the peak absolute value of each detected R-wave and then decays to a specified minimum threshold;

starting a shockable interval timer upon detection of an R-wave;

detecting separate events in the ventricular sensing channel with a specified low shock threshold value and a specified high shock threshold value, wherein the low shock threshold value is lower than the dynamically varying threshold and the high shock threshold value is higher than the dynamically varying threshold;

restarting the shockable interval timer if the sensed ventricular electrogram exceeds the low shock threshold value; and, delivering an atrial defibrillation shock pulse synchronously with a detected R-wave if the shockable interval timer has reached or exceeded a specified minimum value and if the sensed ventricular electrogram value exceeds the high shock threshold value.

2. The method of claim 1 further comprising:

starting the shockable interval timer when a sensed ventricular electrogram value exceeds the low shock threshold value; and, delivering an atrial defibrillation shock pulse synchronously with a detected R-wave if the shockable interval timer has reached or exceeded a specified minimum value and if the sensed ventricular electro gram value exceeds both the dynamically varying threshold value and the high shock threshold value within a specified maximum time interval.

3. The method of claim 1 wherein the dynamically varying threshold value decays exponentially.

4. The method of claim 1 wherein the specified low and high threshold values are specified percentages of a specified minimum value for the dynamically varying threshold.

5. The method of claim 1 further comprising dynamically adjusting the gain of the ventricular sensing channel.

6. The method of claim 1 wherein an episode of atrial fibrillation or other tachyarrhythmia is detected by detecting atrial depolarizations wit an atrial sensing channel and determining an atrial rate therefrom.

7. The method of claim 1 further comprising detecting a ventricular tachyarrhythmia when a ventricular rate exceeds a specified limit value, with the ventricular rate determined as the interval between R-waves detected when a sensed ventricular electrogram value exceeds the dynamically varying threshold value.

8. An apparatus for delivering atrial defibrillation therapy, comprising:

means for detecting an episode of atrial fibrillation or other atrial tachyarrhythmia;

means for detecting ventricular depolarizations (R-waves) with a ventricular sensing channel, wherein R-waves are detected when a sensed ventricular electrogram value exceeds a dynamically varying threshold value, wherein the dynamically varying threshold value is set to a specified percentage of the peak absolute value of each detected R-wave and then decays to a specified minimum threshold;

means for starting a shockable interval timer upon detection of an R-wave;

means for detecting separate events in the ventricular sensing channel with a specified low shock threshold value and a specified high shock threshold value, wherein the low shock threshold value is lower than the dynamically varying threshold and the high shock threshold value is higher than the dynamically varying threshold;

means for restarting the shockable interval timer if the sensed ventricular electrogram exceeds the low shock threshold value; and, means for delivering an atrial defibrillation shock pulse synchronously with a detected R-wave if the shockable interval timer has reached or exceeded a specified minimum value and if the sensed ventricular electrogram value exceeds the high shock threshold value.

9. The apparatus of claim 8 further comprising means for starting the shockable interval timer when a sensed ventricular electrogram value exceeds a specified low threshold value, and to deliver an atrial defibrillation shock pulse synchronously with a detected R-wave if the shockable interval timer has reached or exceeded a specified minimum value and if the sensed ventricular electrogram value exceeds both the dynamically varying threshold value and the high shock threshold value within a specified maximum time interval.

10. The apparatus of claim 8 wherein the dynamically varying threshold value decays exponentially.

11. The apparatus of claim 8 wherein the specified low and high threshold values are specified percentages of a specified minimum value for the dynamically varying threshold.

12. The device of claim 8 wherein the means for detecting an episode of atrial fibrillation or other tachyarrhythmia is an atrial sensing channel which detects atrial depolarizations from which an atrial rate can be determined.

13. The apparatus of claim 12 further comprising means for dynamically adjusting the gain of a sense amplifier in the atrial sensing channel.

14. The apparatus of claim 8 thither comprising means for detecting a ventricular tachyarrhythmia when a ventricular rate exceeds a specified limit value, with the ventricular rate determined as the interval between R-waves detected when a sensed ventricular electrogram value exceeds the dynamically varying threshold value.

15. A cardiac rhythm management device, comprising:

an atrial sensing channel for detecting atrial depolarizations (P waves); and;

a ventricular sensing channel for detecting ventricular depolarizations (R-waves);

a shock pulse generator for generating atrial defibrillation shock pulses;

a controller for controlling the operation of the device, wherein the controller is programmed to detect R-waves when a sensed ventricular electrogram value exceeds a dynamically varying threshold value and to detect separate events in the ventricular sensing channel with a specified low shock threshold value and a specified high shock threshold value, wherein the low shock threshold value is lower than the dynamically varying threshold and the high shock threshold value is higher than the dynamically varying threshold; and, wherein the controller is programmed to detect episodes of atrial fibrillation or other atrial tachyarrhythmias from detected P waves, and, upon detection of an atrial tachyarythmia, to:

start a shockable interval timer upon detection of an R-wave;

restart the shockable interval timer if the sensed ventricular electrogram exceeds the low shock threshold value; and, deliver an atrial defibrillation shock pulse synchronously with a detected R-wave if the shockable interval timer has reached or exceeded a specified minimum value and if the sensed ventricular electrogram value exceeds both the dynamically varying threshold value and the high shock threshold value within a specified maximum time interval.

16. The device of claim 15 wherein the specified low and high threshold values are specified percentages of a specified minimum value for the dynamically varying threshold.

17. The device of claim 15 wherein the gain of a sense amplifier in the atrial sensing channel is dynamically adjusted.

* * * * *

UNITED STATES PATENT AND TRADEMARK OFFICE
CERTIFICATE OF CORRECTION

| | | |
|---|---|---|
| PATENT NO. | : 7,209,785 B2 | Page 1 of 1 |
| APPLICATION NO. | : 10/608518 | |
| DATED | : April 24, 2007 | |
| INVENTOR(S) | : Kim et al. | |

It is certified that error appears in the above-identified patent and that said Letters Patent is hereby corrected as shown below:

On the face page, in field (74), in "Attorney, Agent, or Firm", in column 2, line 2, after "Woessner," insert -- & --.

In column 7, line 30, in Claim 2, delete "electro gram" and insert -- electrogram --, therefor.

In column 7, line 43, in Claim 6, delete "wit" and insert -- with --, therefor.

In column 8, line 37 (Approx.), in Claim 14, delete "thither" and insert -- further --, therefor.

In column 8, line 65, in Claim 15, delete "tachyarrythmia," and insert -- tachyarrhythmia, --, therefor.

Signed and Sealed this

Seventeenth Day of July, 2007

JON W. DUDAS
*Director of the United States Patent and Trademark Office*